(12) United States Patent
De Rosa et al.

(10) Patent No.: US 11,878,030 B2
(45) Date of Patent: *Jan. 23, 2024

(54) OPHTHALMIC FORMULATIONS COMPRISING COOPERATIVE COMPLEXES OF LOW- AND HIGH-MOLECULAR-WEIGHT HYALURONIC ACID

(71) Applicant: Altergon S.A., Lugano (CH)

(72) Inventors: Mario De Rosa, Lugano (CH); Chiara Schiraldi, Lugano (CH)

(73) Assignee: Altergon S.A., Lugano (CH)

( * ) Notice: Subject to any disclaimer, the term of this patent is extended or adjusted under 35 U.S.C. 154(b) by 112 days.

This patent is subject to a terminal disclaimer.

(21) Appl. No.: 17/458,798

(22) Filed: Aug. 27, 2021

(65) Prior Publication Data

US 2021/0386776 A1 Dec. 16, 2021

Related U.S. Application Data

(63) Continuation of application No. 15/747,157, filed as application No. PCT/EP2016/066639 on Jul. 13, 2016, now abandoned.

(30) Foreign Application Priority Data

Jul. 28, 2015 (IT) .................. 102015000038988

(51) Int. Cl.
| | | |
|---|---|---|
| *A61K 31/728* | (2006.01) | |
| *A61K 31/726* | (2006.01) | |
| *A61P 27/04* | (2006.01) | |
| *A61K 9/00* | (2006.01) | |

(52) U.S. Cl.
CPC .......... *A61K 31/728* (2013.01); *A61K 9/0048* (2013.01); *A61K 31/726* (2013.01); *A61P 27/04* (2018.01)

(58) Field of Classification Search
None
See application file for complete search history.

(56) References Cited

U.S. PATENT DOCUMENTS

| 5,166,331 A | 11/1992 | Valle et al. |
| 5,770,628 A | 6/1998 | Cantoro |
| 2007/0059276 A1 | 3/2007 | Bergman et al. |
| 2013/0129844 A1 | 5/2013 | Claret et al. |
| 2013/0143838 A1 | 6/2013 | Sanchez et al. |
| 2013/0156867 A1 | 6/2013 | Claret et al. |

FOREIGN PATENT DOCUMENTS

| EP | 2070518 A2 | 6/2009 |
| EP | 2596796 A1 | 5/2013 |
| WO | 2012032151 A2 | 3/2012 |
| WO | 2013174863 A1 | 11/2013 |

OTHER PUBLICATIONS

Bhojiwani R. et al. "Treatment of dry eye: an analysis of the British Sjogren Syndrome association comparing substitute tear viscosity and subjective efficacy," Contact Lens & Anterior Eye, vol. 34, pp. 269-273 (2011).
D'Agostino A., et al., "In vitro analysis of the effects on wound healing of high- and low-molecular weight chains of hyaluronan and their hybrid H-HA/L0HA complexes," BMC Cell Biology (2015) 16:19.
European Pharmacopoeia 7.0 Jan. 2008.
Freire V et al., "Corneal wound healing promoted by 3 blood derivatives; an in vitro and in vivo comparative study", Cornea, vol. 33, No. 6, pp. 614-620 (2014).
Goulet E., et al. "Prefilled syringe sterilization—No. 2 sterilization; a flexible solution for prefilled syringes", Drug Development & Delivery, Oct. 2014.
Ixium HCS (LCA product) published Jan. 6, 2009.
Jun Woong Moon, et al., "Short term effect of topical cyclosporine and viscoelastic on the ocular surfaces in patients with dry eye", Korean Journal of Ophthalmology 21(4):189-194 2007.
Imberg, M.B., et al., "Topical application of hyaluronic acid and chondroitin sulfate in the treatment of dry eyes," American Journal of Ophthalmology 103:194-197, 1987.
Miyauchi S. et al., "Hyaluronan and chondroiting sulfate in rabbit tears", Curr Eye Res; Feb. 1996; 15(2): 131-5.
Nepp J et al., "The clinical use of viscoelastic artificial tears and sodium chloride in dry-eye syndrome", Biomaterials, vol. 22, pp. 3305-3310 (2001).
Nepp J. , et al., "The clinical use of viscoelastic artificial tears and sodium chloride in dry-eye syndrome", Biomaterials 22 (2001), 3305-3310.
Power point presentation of Masoud Jafari et al., Dec. 5, 2012.
Search Report and Written Opinion of PCT/EP2016/066639 dated Sep. 26, 2016.
Third party observation on corresponding EP patent Application No. 3328396 of Apr. 16, 2019.

*Primary Examiner* — Leigh C Maier
(74) *Attorney, Agent, or Firm* — SILVIA SALVADORI, P.C.; Silvia Salvadori

(57) ABSTRACT

Disclosed are ophthalmic formulations which use complexes called L/H-HA, obtainable by subjecting at least two fractions of hyaluronic acids and/or other glycosaminoglycans with different molecular weights to an appropriate heat cycle.

4 Claims, No Drawings

OPHTHALMIC FORMULATIONS COMPRISING COOPERATIVE COMPLEXES OF LOW- AND HIGH-MOLECULAR-WEIGHT HYALURONIC ACID

This application is a continuation of U.S. patent application Ser. No. 15/747,157, filed Jan. 24, 2018, which is a U.S. national stage of PCT/EP2016/066639 filed on 13 Jul. 2016, which claims priority to and the benefit of Italian Application No. 102015000038988 filed on 28 Jul. 2015, the contents of which are incorporated herein by reference in their entireties.

The present invention relates to ophthalmic formulations comprising cooperative complexes of low- and high-molecular-weight glycosaminoglycans.

STATE OF THE ART

Disorders of the ocular apparatus are continually increasing due to growing environmental pollution, widespread use of contact lenses, increased resistance to antibiotics by infectious micro-organisms, and the increase in disorders such as diabetes, which causes severe eye damage.

There is consequently growing interest in the development of increasingly effective ophthalmic products, which combat the disorder without causing discomfort for the patient, especially when the medicament has to be applied frequently, on a chronic basis.

Eyedrops play a major role among ophthalmic products, due to their ease of application and their efficacy in certain disorders such as dry eye, which is highly incapacitating for the patient.

The most widely used ophthalmic preparations are eyedrops, which consist of a sterile aqueous or oily suspension or solution containing one or more active ingredients and various additives and rheological ingredients. Eyedrops are instilled into the lower conjunctival sac, and represent the preferred pharmaceutical form for the treatment of eye disorders of various aetiologies, such as dry eye, inflammation, infection, irritation, glaucoma and conjunctivitis, and for use before diagnostic procedures or after surgical operations.

Eyedrops contain the following types of excipient:

1) Tonicity adjusters—Eyedrops must normally be isotonic with the lacrimal fluid. An ophthalmic solution is considered isotonic when its tonicity is equal to that of a saline solution (0.9% w/w sodium chloride). Sodium chloride is the most widely used tonicity adjuster, but the eye also tolerates other compounds, provided that their tonicity is equivalent to that of sodium chloride concentrations ranging between 0.5% and 1.8% w/w.

2) Viscosity-controlling agents—Viscosity control in an ophthalmic formulation plays a strategic role in the efficacy of the product because preparations with low viscosity reduce the bioavailability of the active substances, due to the shorter residence time of the product on the eye surface, caused by blinking, during which it is estimated that there is a shear rate of 20000 s$^{-1}$, and by its passage through the nasolacrimal duct. Polymers such as hyaluronic acid, polyacrylates, chitosan, cellulose derivatives, pectins, alginate, polyvinyl alcohol, polyvinylpyrrolidone, etc. are usually employed to control viscosity and mucoadhesion. In the design of an ophthalmic formulation, the viscosity must not exceed 30 mPa·s, to prevent discomfort caused by excessive resistance of the viscous solution to the movement of the eyelids, and blurred vision. Factors such as the hydration, molecular weight, shape and concentration of the polymer, and the presence of particular functional groups on the chain, strongly influence the mucoadhesion of the formulation, which is mainly generated by a process of molecular entanglement between the polymer chains and the macromolecular component of the mucous layer, especially mucin. The minimum length of the polymer chain of the viscosity-controlling agent must therefore be at least 100 KDa, and macromolecular ingredients with strong crosslinking, which prevent effective entanglement, should not be used. In general, the greater the flexibility of the polymer chain of the viscosity-controlling agent, the greater its spread in the mucous layer and entanglement with mucin, both of which factors combine to generate high mucoadhesion, ensuring the optimum residence time of the product applied to the eye surface.

3) pH stabilisers—The purpose of these excipients is to keep the product isohydric with the lacrimal fluid. Ophthalmic preparations with a pH below 4 or above 10 cause irritation and intense lacrimation, especially when the pH is strongly alkaline. When choosing the type of buffer to be added to the ophthalmic formulation, the stability of the active ingredient at physiological pH values should be borne in mind, because drugs like pilocarpine, used in the treatment of glaucoma, require a pH of 4-5 to ensure adequate chemical stability of the molecule.

4) Preservatives—Used to guarantee that the sterility of the formulation is maintained, this being a crucial requirement for ophthalmic preparations. This type of excipient is only used in multi-dose formulations, because once the container is opened, sterility is not guaranteed over time. Examples of preservatives are phenethyl alcohol, chlorhexidine acetate, chlorhexidine gluconate, chlorobutanol, benzalkonium chloride, phenylmercuric nitrate, etc. However, as all those preservatives generally have an adverse impact on the eye surface, they are now tending to be eliminated from multi-dose systems that use particular dispensing systems, equipped with a filter that isolates the ophthalmic solution from the external environment when the product is used.

5) Solubilisers and suspending agents—Used for formulations in suspension when the active ingredient is poorly soluble. Examples of such products are polysorbates, sodium lauryl sulphate and sorbitan monoleate.

Hyaluronic acid and the salts thereof, known as hyaluronans (hereinafter collectively called "HA"), is widely used to prepare ophthalmic products due to its viscosity-controlling, mucoadhesive and hydrating action.

The pseudoplastic behaviour of HA is particularly important, as it leads to high viscosity values at rest and low viscosity values during rapid blinking, an ideal characteristic to reduce resistance to eyelid movements during blinking, at the same time ensuring that the product remains on the eye surface for a sufficient time. Numerous studies demonstrate that the use of HA in ophthalmic formulations increases the residence time in the pre-corneal area of numerous active ingredients, such as pilocarpine, timolol, aceclidine (glaucoma treatment), tropicamide (a mydriatic agent), arecoline (a mitotic agent), gentamicin and tobramycin (antimicrobials) (Yong-Hong Liao et al., Hyaluronan: Pharmaceutical Characterization and Drug Delivery 2005, Vol. 12, No 6. Pages 327-342). HA solutions are successfully used as artificial tears in cases of dry eye, due to the ability of the polymer to bind water and epithelial cells, thus considerably increasing the stability of the lacrimal fluid, especially in cases where the mucin component is deficient. Examples of ophthalmic products containing HA, designed to supplement a tear secretion which is deficient due to mechanical, environmental or visual stress and to restore the physiological conditions of the tear film, are Blugel® and Bluyal®, two eyedrop brands consisting of HA and N-hydroxymethylglycinate combined with sodium edetate as preservative; Hyalistil® and Irilens®, used to improve the tolerability of contact lenses and in the symptomatic treatment of dry eye syndrome; Artelac Splash®, a soothing, hydrating, revitalising product used for dry, tired, irritated, red eyes; and Nebuvis®, a lubricant for tired, red eyes, used in case of poor lacrimation, long-term use of contact lenses, time spent in closed, smoky or air-conditioned rooms, and long times spent working at a computer screen.

Despite the undoubted advantages of using HA to prepare ophthalmic formulations, the following problems have not yet been solved:

a) the impossibility of optimising the hydrating capacity of the ophthalmic formulation by using higher HA concentrations, as the limit of 0.5% w/w cannot be exceeded so as not to exceed the viscosity of 30 mPa·s, over which discomfort becomes excessive due to the resistance of the viscous solution to the movement of the eyelids and the resulting blurred vision;

b) the impossibility of circumventing this limit by using low-molecular-weight HA, which is less viscous, because the reduction in molecular weight tends to reduce the mucoadhesion of the formulation due to the lower ability of the shorter HA chains to entangle with mucin;

c) the impossibility of fully exploiting the differentiated biological effects of HA according to molecular weight (Stern R., et al. *Eur. J. Cell Biol.* 2006; 85 (8 Suppl): 699-715), because the use of high- and low-molecular-weight mixtures of HA would lead to a rapid selective loss of the fraction with the lowest molecular weight due to the reduction in mucoadhesion with the length of the polysaccharide chain.

EP 2614090 discloses cooperative complexes of hyaluronic acid with high (H-HA) and low (L-HA) molecular weight, which are useful for intradermal skin biorevitalisation treatments, intraarticular viscosupplementation treatments, intravesical cystitis treatments, and treatments for inflammatory disorders of the vagina, alveolar disorders and disorders of the oral cavity.

HA molecules in solution are characterised by cooperative interaction phenomena based on the formation of hydrophobic bonds and interchain hydrogen bonds. The cooperativity of said interactions depends on the length, and therefore the molecular weight of the chains. The long chains of H-HA give stable interactions with one another, which affect all the molecules present in solution, giving rise to a three-dimensional network, whereas L-HA molecules give less stable interactions, which lead to aggregation systems that do not simultaneously involve all the molecules present, which interact with one another in clusters. This different type of aggregation of H-HA and L-HA in solution is responsible for very different rheological behaviours, such as viscosity, a very important property for numerous applications, especially in the medical field. The rapid decline in the viscosity of HA solutions according to molecular weight depends on this different intermolecular interaction capacity due to which, concentration being equal, the viscosity of H-HA solutions with a molecular weight greater than $1·10^6$ Da is orders of magnitude greater than those of L-HA solutions with a molecular weight ranging between $5·10^3$ and $5·10^5$ Da.

Said L/H-HA cooperative complexes are formed by subjecting aqueous solutions containing both H-HA and L-HA to a suitably configured heat cycle. Solutions of L/H-HA cooperative hybrids are characterised by viscosities that do not change over time and are considerably lower than those before the heat cycle, wherein energy conditions are created which are able to simultaneously break all the interactions between the H-HA chains and those between the L-HA chains. Under said conditions the pre-requisites no longer exist for the weak interactions that develop between the molecules in solution to be cooperative, and the polymer chains act as independent entities. Subsequently, when the solution is cooled during the heat treatment cycle, interchain interactions increasingly start to re-form, and in this case develop statistically between all the HA molecules present in solution, whether of high or low molecular weight, giving rise to hybrid systems that stabilise when, due to the increase in the number of weak intermolecular bonds and their cooperativity, the interaction system established between the polymer chains with different molecular weights is no longer modifiable over time. The validity of this mechanism is demonstrated by the fact that when two solutions, one of L-HA and one of H-HA, are subjected separately to the heat cycle and then mixed together after cooling, the concentration of the species in solution being equal, the drastic, immediate reduction in viscosity attributed to the formation of the hybrid system is not observed, as it can only form if the two molecular species are simultaneously present during the heat cycle. The molecular weight of the HAs used and the relative ratio between L-HA and H-HA critically influence the rheological characteristics of the L/H-HA complex that forms; the greater the difference in molecular weight between the L-HA and H-HA used, and the higher the ratio between L-HA and H-HA, the greater the reduction in viscosity of the hybrid system.

Complexes of the same type of L/H-HA can be obtained by replacing L-HA with other low-molecular-weight glycosaminoglycans (15-150 KDa) such as chondroitin sulphate (CS), keratan sulphate (KS) and chondroitin (C).

DESCRIPTION OF THE INVENTION

It has now been found that said hybrid cooperative complexes of high- and low-molecular-weight glycosaminoglycans known from EP 2614090 allow the preparation of ophthalmic formulations having specific advantages.

The invention therefore relates to ophthalmic formulations comprising, as active ingredients, hybrid cooperative complexes (L/H-HA) obtainable by heating, at 100-130° C. for 10-30 min, a mixture of aqueous solutions of at least one fraction (L-HA) of hyaluronic acid or of chondroitin sulphate, keratan sulphate or chondroitin (CS, KS, C), said fraction having an average molecular weight ranging between $1·10^4$ and $5·10^5$ Da, and an aqueous solution of at least one fraction (H-HA) of hyaluronic acid having an average molecular weight at least 5 times higher than that of L-HA and in any event ranging between $5·10^4$ Da and $5·10^6$ Da, the weight ratio between L-HA and H-HA in the L/H-HA complex ranging between 0.5 and 2.

The average molecular weight of the H-HA fraction preferably ranges between $5·10^5$ Da and $3·10^6$ Da, while the average molecular weight of the L-HA fraction preferably ranges between $3·10^4$ Da and $1·10^5$ Da.

If the low-molecular-weight fraction does not consist of hyaluronic acid but of other glycosaminoglycans, its average molecular weight preferably ranges between $1·10^4$ and $1·10^5$ Da.

The formulations according to the invention, typically in the form of eyedrops, ointments or sprays, preferably contain water as solvent, and are characterised by a viscosity not exceeding 100 mPa s, preferably not exceeding 30 mPa·s.

The concentration of the complexes as defined above in the formulations according to the invention can range from 0.1 to 1% by weight.

The formulations according to the invention can include other active ingredients in ophthalmic use (non-steroidal anti-inflammatory drugs, antibiotics, beta-blockers, antihistamines, etc.), buffer systems, salts, osmoregulators, preservatives, soothing agents and rheological reagents.

The formulations according to the invention are particularly useful as tear substitutes for the treatment of dry eye syndrome.

The use of cooperative L/H-HA complexes and their structural analogues wherein L-HA is replaced by other low-molecular-weight glycosaminoglycans such as CS, KS and C presents the following advantages over conventional formulations based on H-HA:

a) the viscosity of the formulation can be varied continuously by modulating the molecular weight and the relative ratio of the HA species used to form the L/H-HA complex;

b) this in practice makes the HA concentration independent of the viscosity of the solution and improves the hydrating and lubricating action of the ophthalmic formulation, increasing the quantity of HA used as L/H-HA complex without exceeding the limit of 30 mPa·s over which, in the presence of high viscosity, excessive discomfort is caused by the resistance of the solution to the movement of the eyelids and the resulting blurred vision;

c) the biological effects associated with the simultaneous use of HA with different molecular weights can be optimised, because in contact with the eye surface, the L/H-HA complexes act as slow-release systems of L-HA and H-HA; high mucoadhesion is guaranteed although a fraction of L-HA is present which, taken individually, is less mucoadhesive due to its low molecular weight;

d) surprisingly, tests on cell dehydration stress models demonstrate that the L/H-HA complexes are far superior to H-HA alone in functional terms.

e) tests on volunteers demonstrate the superiority of the formulation according to the invention over conventional ophthalmic formulations based on H-HA.

The invention is illustrated in detail in the examples set out below.

Example 1—Preparation of Ophthalmic Formulations Based on L/H-HA Complexes with Variable Stoichiometry and Predetermined Viscosity 4 ophthalmic formulations with an aqueous base are prepared which have L/H-HA complexes of different compositions as active ingredient and rheological component. H-HA (MW 1.36·10$^6$ Da; Mw/Mn 1.43) and L-HA (MW 8.41·10$^4$ Da; Mw/Mn 1.75) are dissolved in 100 mL of water in the quantities reported in Table 1. The resulting solutions, all of which contain the same quantity of H-HA and increasing quantities of L-HA, undergo the following heat cycle in a pressurised system: from 20° C. to 120° C. in 12 min, for 1 min at 120° C., from 120° C. to 20° C. in 15 min. The dynamic viscosity of the samples, the MW and polydispersity index Mw/Mn of L-HA, H-HA and L/H-HA are determined with the Viscotek system described in detail below. The data in Table 1 demonstrates that the viscosity of the L/H-HA cooperative complexes depends on the L-HA/H-HA ratio; the higher the ratio, the lower the viscosity. In any event the most important variation in η takes place with the formation of the L/H-HA complex, which is already significant as from the lowest value of the ratio (L-HA/H-HA w/w). Ophthalmic formulations comprising the L/H-HA complexes described can be used to prepare novel eyedrops wherein the total quantity of HA can be varied simply, without causing discomfort for the patient.

TABLE 1

Measurement of dynamic viscosity η of hybrid cooperative complexes L/H-HA with a different L-HA/H-HA ratio. The measurements of η are taken immediately after the heat treatment.

| Sample of L/H-HA (L-HA/H-HA w/w) | L-HA (g in 100 mL of water) | H-HA | Treatment 120° C. 12 min. η* (Pa · s) | $\eta_{H\text{-}HA}/\eta_{L/H\text{-}HA}$ |
|---|---|---|---|---|
| 0.0 | 0.0 | 1.0 | 5.428 | — |
| 0.5 | 0.5 | 1.0 | 0.066 | 82.24 |
| 1.0 | 1.0 | 1.0 | 0.040 | 135.70 |
| 1.5 | 1.5 | 1.0 | 0.035 | 155.03 |

*The measurements of η are taken immediately after mixing.

Viscotek measurements—the MW and polydispersity index Mw/Mn are determined with a size-exclusion chromatography system equipped with a multi-detector, consisting of a four-bridge viscometer, a refractometer, a right-angle light-scattering detector (RALS) and a low-angle light-scattering detector (LALS), made by Viscotek (www.viscotek.com). The signal measured with LALS is proportional to the molecular weight and concentration, and the signal measured with the viscometric detector is proportional to the concentration of the sample and the intrinsic viscosity, while the refractometer measures the concentration. The Viscotek apparatus not only determines the molecular weight of HA, but also allows evaluation of the degree of heterogeneity of the molecular weight in the population of molecules present, described by the polydispersity index Mw/Mn, automatically calculated by the Viscotek apparatus, and defined as the ratio between the average molecular weight (Mw=$\Sigma_i m_i M_i/\Sigma_i m_i$ wherein $m_i$ is the mass of polymer with molecular weight $M_i$ and $\Sigma_i m_i$ is the total mass of the polymer, which expression, taking $m_i=n_i M_i$, can also present as Mw=$\Sigma_i n_i M_i^2/\Sigma_i n_i M_i$) and the weight average molecular weight (Mn=$\Sigma_i n_i M_i/\Sigma_i n_i$ wherein $n_i M_i$ is the mass of polymer with molecular weight $M_i$ and $\Sigma_i n_i$ is the total number of moles of polymer present).

The measurements of dynamic viscosity η are conducted with an Anton Paar Physica MCR 301 rheometer, using coaxial geometry. η is determined at 25° C. at a constant shear rate (γ'=2 s$^{-1}$) which falls into the Newtonian viscosity range of the polymer solution (η is constant relative to γ', and only depends on the conformation of the polymer in solution). The dynamic viscosity measurements as a function of the shear rate are measured in a range from 0.1 s$^{-1}$ to 1000 s$^{-1}$, acquiring 50 points in "no time setting" mode for each measurement.

Example 2—Preparation of Ophthalmic Formulations Comprising L/H-HA Complexes with Different Molecular Weight Values of L-HA and H-HA and Predetermined Viscosity 4 ophthalmic formulations with an aqueous base are prepared which have, as active ingredient and rheological component, L/H-HA complexes with the same 1:1 w/w ratio between H-HA and L-HA but use L/HA of a different molecular weight. Aqueous solutions of H-HA (MW 1.36·10⁶ Da; Mw/Mn 1.43) and L-HA (MW 8.41·10⁴ Da; Mw/Mn 1.75); L-HA (MW 2.12·10⁵ Da; Mw/Mn 1.61) are prepared at the concentration of 2% w/v in distilled water, and used to prepare the various solutions reported in Table 2. The resulting solutions undergo the following heat cycle in a pressurised system: from 20° C. to 120° C. in 12 min, for 1 min at 120° C., from 120° C. to 20° C. in 15 min. The dynamic viscosity η of the samples, the MW and the polydispersity index Mw/Mn of L-HA, H-HA and L/H-HA are determined as described in Example 1.

The data in Table 2 demonstrates that, all the other parameters being equal, the lower the MW of the L-HA used to form the L/H-HA complex, the greater the reduction in η. In the comparison between the η values of hybrid complexes L/H-HA using L-HA with MW 8.41·10⁴ Da or 2.20·10⁵ Da, the value of the $\eta_{H\text{-}HA}/\eta_{L/H\text{-}HA}$ ratio increases about 50 times.

TABLE 2

Measurement of dynamic viscosity η of L/H-HA complexes with L-HA/H-HA ratio of 1 w/w, constructed with L-HA of different MWs. The measurements of η are taken immediately after the heat treatment.

| Sample | 2% w/v sol. (mL) H-HA | 2% w/v sol. (mL) L-HA | H₂O (mL) | Heat treatment 120°; 10 min η (Pa · s) | $\eta_{H\text{-}HA}/\eta_{L/H\text{-}HA}$ |
|---|---|---|---|---|---|
| H-HA | 100 | 0 | 100 | 5.428 | — |
| L-HA 8.41 · 10⁴ Da | 0 | 100 | 100 | 0.001 | — |
| L-HA 2.20 · 10⁵ Da | 0 | 100 | 100 | 0.016 | — |
| L/H-HA 8.41 · 10⁴ Da | 100 | 100 | 0 | 0.040 | 135.70 |
| L/H-HA 2.20 · 10⁵ Da | 100 | 100 | 0 | 1.834 | 2.96 |

The data in Table 2 demonstrates that the viscosity of the cooperative complexes L/H-HA depends on the molecular weight of the L-HA used to form the complex; the lower the MW of L-HA, the lower the viscosity of the complex. If this concept is generalised, the greater the difference in MW between H-HA and L-HA, the greater will be the value of $\eta_{H\text{-}HA}/\eta_{L/H\text{-}HA}$. Ophthalmic formulations comprising the L/H-HA complex described in this example can be used to prepare novel eyedrops wherein the quantity of HA can be increased, without reaching η values that cause discomfort for the patient, by using H-HA and L-HA pairs with a greater difference in MW.

Example 3—Preparation of Ophthalmic Formulations Comprising Cooperative Complexes Between H-HA and Glycosaminoglycans with Low Molecular Weight 4 ophthalmic formulations with an aqueous base are prepared which have complexes between H-HA and glycosaminoglycans with low molecular weight as active ingredient and rheological component. H-HA (MW 1.36·10⁶ Da; Mw/Mn 1.43), L-HA (MW 8.41·10⁴ Da; Mw/Mn 1.75), CS (MW 3.81·10⁴ Da; Mw/Mn 1.65), KS (MW 3.45·10⁴ Da, Mw/Mn 1.52), C (Mw 2.9·10⁴ Da Mw/Mn 1.66) are dissolved in 100 mL of water in the quantities reported in Table 3. The resulting solutions, all of which contain the same quantity of H-HA, and contain low-molecular-weight L-HA, CS, KS or C, as component, undergo the following heat cycle in a pressurised system: from 20° C. to 120° C. in 12 min, for 1 min at 120° C., from 120° C. to 20° C. in 15 min. The dynamic viscosities of the samples, the MW and the polydispersity index are determined with the Viscotek system, as reported in detail in Example 1. The data in Table 3 demonstrates that glycosaminoglycans other than L-HA, such as CS, KS and C, form cooperative complexes with H-HA, albeit with a phenomenology involving a reduction in viscosity following the formation of the complex which is less marked than when the low-molecular-weight component is L-HA. Ophthalmic formulations comprising complexes between H-HA and CS or KS or C can be used to prepare eyedrops wherein the total quantity of HA can be varied simply, without causing discomfort for the patient.

TABLE 3

Measurement of dynamic viscosity η of hybrid cooperative complexes L/H-HA, CS/H-HA, KS/H-HA and C/H-HA characterised by a 1:1 w/w stoichiometry between low-molecular-weight glycosaminoglycan and H-HA. The measurements of η are taken immediately after the heat treatment.

| Sample of L/H-HA (L-HA/H-HA w/w) | L-HA (g in 100 mL of water) | H-HA | Treatment 120° C. 12 min. η* (Pa · s) | $\eta_{H\text{-}HA}/\eta_{X^{**}/H\text{-}HA}$ |
|---|---|---|---|---|
| H-HA | 0.0 | 1.0 | 5.428 | — |
| L/H-HA | 1.0 | 1.0 | 0.066 | 82.24 |
| CS/H-HA | 1.0 | 1.0 | 1.543 | 3.51 |
| KS/H-HA | 1.0 | 1.0 | 1.584 | 3.42 |
| C/H-HA | 1.0 | 1.0 | 0.781 | 6.95 |

*The measurements of η are taken immediately after mixing.
**X= CS or KS or C.

Example 4—Mucoadhesion of the L/H-HA Complexes Referred to in Examples 1 and 2

Mucoadhesion is determined as reported by Hassan et al. (1990, *Pharm Res. May;* 7(5):491-5) and Oechsner et al. (1999, Eur J Pharm Biopharm. March; 47(2): 113-8).

Sigma mucin M2378 PCode 1001622405 is used.

The following solutions are prepared, and their viscosity measured:
1) first, a suspension of 15% (w/w) mucin in sterile water, which has a pH of about 3.8-4.0, corrected to 7.4 by adding 0.35 M Na₃PO₄. The neutral solution is then diluted with water to 10% w/w.
2) a polymer solution whose mucoadhesion is to be evaluated in phosphate buffer at pH 7.4;
3) a mixture containing 10% w/w mucin and polymer so that the polymer has a final concentration equal to that of solution 2.

A polymer can be described as mucoadhesive if the viscosity value of the solution containing the polymer and the mucin (solution 3) is greater than the sum of the viscosities of the polymer solution (solution 2) and the mucin solution (solution 1). This increase in viscosity is attributable to the polymer-mucin interaction; the extent of that increase indicates the mucoadhesive strength of the polymer (2015, Biomacromolecules. March 9; 16(3):924-35. doi: 0.1021/bm501832y. Epub 2015 Feb. 18).

When the three solutions are prepared, it is important to maintain the pH in the 7.0-7.6 range and the conductivity in the 12.0-14.0 mScm⁻¹ range, to ensure that variations in those pH and conductivity ranges do not significantly affect the viscosity of the solutions analysed.

Mucoadhesion is calculated in terms of Δ % using the following formula:

$$\Delta(\%) = [\eta_{muc+HA} - (\eta_{muc} + \eta_{HA})]/(\eta_{muc} + \eta_{HA}) * 100$$

Wherein:

$\eta_{muc+HAS}$ is the viscosity of the solution containing both mucin and HA (solution 3);

$\eta_{muc}$ is the viscosity of the solution of mucin only (solution 1);

$\eta_{HA}$ is the viscosity of the solution of HA only (solution 2).

The viscosity measurements are taken on 8 mucin solutions prepared independently.

The solutions of H-HA (MW 1.36·10$^6$ Da; Mw/Mn 1.43), L-HA (MW 8.41·10$^4$ Da; Mw/Mn 1.75) and L/H-HA 1:1 w/w, obtained by using the above-mentioned H-HA and L-HA, are prepared by dissolving the sample in phosphate buffer at a pH of 7.4. The phosphate buffer used is prepared by adding 0.5M HCl to an 0.35 M solution of Na$_3$PO$_4$ until a pH of 7.4 is reached, to give a salt concentration similar to that of the mucin solution (solution 1).

The H-HA solutions are prepared at 0.15, 0.23, 0.28 and 0.30% w/w, and the L-HA and L/H-HA solutions are prepared at 0.15, 0.30, 0.45, 0.80 and 1.03% w/w; each solution is prepared in duplicate.

A concentrated solution of the HA sample in water is added to the buffered mucin solution to obtain, after mixing, HA at the concentration of solution 2. The solution is made up to the graduation mark with water. Each solution is prepared in duplicate.

Table 4 shows the Δ % values for solutions of H-HA, L-HA and the L/H-HA complex at the same concentration value (0.30%) and at two different shear rate values (33.9 and 222.2 s$^{-1}$).

Table 5 shows the Δ % values for solutions of H-HA, L-HA and the L/H-HA complex at concentrations with the same dynamic viscosity value (η).

TABLE 4

Mucoadhesion index (Δ%) at two H-HA shear rate values (MW 1.36 · 10$^6$ Da; Mw/Mn 1.43), L-HA (MW 8.41 · 10$^4$ Da; Mw/Mn 1.75) and L/H-HA, stoichiometry L-HA/H-HA 1:1 w/w, all at the same concentration (0.30% w/w).

| Shear rate (s$^{-1}$) | Mucoadhesion index (Δ%) | | |
|---|---|---|---|
| | H-HA 0.30% w/w | L-HA 0.30% w/w | L/H-HA 0.30% w/w |
| 33.9 | 269 | 107 | 253 |
| 222.2 | 153 | 81 | 142 |

TABLE 5

Mucoadhesion index (Δ%) at shear rate 33.9 s$^{-1}$ of H-HA (MW 1.36 · 10$^6$ Da; Mw/Mn 1.43), L-HA (MW 8.41 · 10$^4$ Da; Mw/Mn 1.75) and L/H-HA stoichiometry L-HA/H-HA 1:1 w/w, at concentrations having the same viscosity value (η).

| Shear rate (s$^{-1}$) | Mucoadhesion index (Δ%) | | |
|---|---|---|---|
| | H-HA 0.30% w/w | L-HA 1.12% w/w | L/H-HA 0.6% w/w |
| 33.9 | 269 | 320 | 330 |

The data in tables 4 and 5, taken as a whole, demonstrates that: a) concentration being equal, H-HA is the most mucoadhesive form of the biopolymer in a wide shear rate range (3-200 s$^{-1}$), while at higher values the mucoadhesion values of the various forms become comparable; b) dynamic viscosity being equal, L/H-HA and L-HA are more mucoadhesive than H-HA throughout the shear rate range.

Example 5—Evaluation of Biological Response on Porcine Primary Corneal Cells: Wound-Healing Analysis Preparation of primary corneal epithelial cell cultures from porcine eye—The eyes of mini-pigs used for surgical training are removed at the time of euthanasia, and the corneas are removed. The corneas are then subjected to enzymatic digestion with a solution of 3 mg/mL collagenase and 4 mg/mL dispase diluted 1:5 in DMEM/F12 culture medium (Dulbecco's Modified Eagle Medium/Nutrient Mixture F-12, GIBCO Invitrogen USA) 15% FBS (GIBCO Invitrogen, USA) under stirring (600 rpm) at 37° C. The medium used for the growth of the porcine corneal epithelial cells is DMEM/F12 with the addition of 15% foetal bovine serum (FBS), 10 ng/mL EGF (epidermal growth factor, GIBCO Invitrogen, USA) and 40μ (g/mL gentamicin sulphate (Fisiopharma, Italy). After 20 h the cells are filtered through 0.70 μm filters and centrifuged at 1500 rpm for 10 min. The pellet is resuspended in culture medium and the cells are seeded to amplify the culture, which mainly consists, 4 days after seeding, of endothelial cells with insignificant fibroblastoid contamination.

Wound-healing test—The biological activity and effect of the L/H-HA complex, prepared as described in Example 1, compared with H-HA alone, is evaluated with a wound-healing test, monitoring the wound-healing process with time-lapse video microscopy (TLVM) wherein the incubator stage is maintained at 37° C. in a 5% CO$_2$ atmosphere. The wound-healing test involves seeding about 1×10$^5$ porcine corneal endothelial cells in each well of a 12-well plate. The cells reach 100% confluency after two days. A wound is created mechanically on the cell monolayer, using a sterile tip (Ø=0.1 mm). The injured cells are treated with: a) 0.3% w/v H-HA (1300-1400 KDa); b) the 0.3% L/H-HA complex, stoichiometry 1:1 w/w H-HA/L-HA; c) the 0.6% L/H-HA complex, stoichiometry 1:1 w/w H-HA/L-HA) in DMEM 1.5% FBS growth medium; the culture medium alone is therefore used as control (CTR).

Comparing a and b provides indications, HA content being equal, regardless of its MW, whereas comparison of a and c analyses two formulations which have the same quantity of H-HA alone. The solutions are sterilised by filtration, using 0.22 μm filters. The plate thus prepared is housed in the incubator stage of the TLVM station, and 5 fields of view are selected for each well, a delay time of 60 min being set. Each test is conducted in triplicate, and the total duration of the experiment is set at 24 h, having observed that complete repair of the wound takes place after about 12 h for all treatments.

The quantitative analysis conducted on the images recorded, obtained with OKO-Vision2009 software (OKO-LAB Italy), shows that treatment with the 0.6% H-HA/L-HA complex leads to 95% wound healing after only 6 h, whereas at the same time, treatment with lower concentrations than the 0.3% H-HA/L-HA complex and with 0.3% H-HA alone produce wound healing of 70% and 62% respectively. The cells not treated with HA (CTR) only present 50% healing after 6 h.

Example 6—Tests on Cell Model of Corneocytes from Porcine Eye Explants: an In Vitro Model of Dry Eye Syndrome A suspension containing 5×10$^4$ corneal cells from mini-pig explants, prepared as described in Example 4, is seeded in each well of a 24-well plate, and the cells, grown in DMEM 15% FBS medium, reach 70% confluency after one day at 37° C. in an atmosphere containing 5% $CO_2$. The cells are treated for 2 h with 0.3% w/w H-HA and the 0.6% w/w H-HA/L-HA complex used in the ratio of 1:1 w/w H-HA and L-HA as shown in Table 1. In the test, the solutions are used "as is" and diluted 1:3, 1:10 and 1:30. All solutions are prepared in the corneal growth medium. After treatment, the cells are subjected to dehydration stress, being incubated dry and without a lid at 37° C. for 20 min. The positive control (CTR) is represented by the cells not subjected to dehydration, while the negative control (NC) cells undergo dehydration, but not protective pre-treatment with H-HA or L/H-HA.

At the end of the trial, cell viability is determined with the Presto Blue viability assay (Invitrogen, GIBCO), conducted by adding 1 mL of a solution of Presto Blue diluted 1:10 in growth medium to each well. The presence of metabolically active cells is demonstrated by the conversion of the Presto Blue reagent (blue resazurin) to a fuchsia-coloured compound (resorufin). The spectrophotometric readings at 570 nm (maximum absorption peak for resazurin) and 600 nm (maximum absorption peak for resorufin) allow cell viability to be quantified on the basis of the number of cells able to activate the reaction. All the samples at the different concentrations were assayed in triplicate. The results, expressed as percentage cell viability compared with the positive control, demonstrate that pre-treatment with the L/H-HA complex guarantees better protection of the corneal cell layer than pre-treatment with H-HA, and this difference is accentuated when the active ingredient is diluted: NC (48%), 0.3% H-HA (94%) and 0.6% L/H-HA (98%); NC (56%), 0.1% H-HA (80%) and 0.2% L/H-HA (100%); NC (40%), 0.03% H-HA (52%) and 0.06% L/H-HA (98%); NC (45%), 0.001% H-HA (48%) and 0.002% L/H-HA (62%).

Example 7—Ophthalmic Formulations Comprising L/H-HA Complexes

Eyedrops 1—0.6% w/w L/H-HA complex (stoichiometry L-HA/H-HA 1.5:1 w/w, prepared as reported in Example 1, in aqueous solution, pH 7.2, for phosphate buffer, final osmolarity 300 $mOsmL^{-1}$, corrected with NaCl or another biocompatible osmolite containing 0.05% w/w PUFA sodium salt.

Eyedrops 2—0.6% w/w L/H-HA complex (stoichiometry L-HA/H-HA 1:1 w/w, prepared as reported in Example 1, in aqueous solution, pH 7.2, for phosphate buffer, final osmolarity 300 $mOsmL^{-1}$, corrected with NaCl or another biocompatible osmolite containing a suitable concentration of an active ingredient with antimicrobial activity commonly used in the ophthalmic field.

Eyedrops 3—0.6% w/w L/H-HA complex (stoichiometry L-HA/H-HA 0.5:1 w/w, prepared as reported in Example 1, in aqueous solution, pH 7.2, for phosphate buffer, final osmolarity 300 $mOsmL^{-1}$, corrected with NaCl or another biocompatible osmolite containing a suitable concentration of an active ingredient with anti-inflammatory activity commonly used in the ophthalmic field.

Eyedrops 4—0.4% w/w C/H-HA complex (stoichiometry C/H-HA 1:1 w/w, prepared as reported in Example 3, in aqueous solution, pH 7.2, for phosphate buffer, final osmolarity 300 $mOsmL^{-1}$, corrected with NaCl or another biocompatible osmolite containing 0.1% w/w cortisone.

Eyedrops 5—0.3% w/w KS/H-HA complex (stoichiometry KS/H-HA 1:1 w/w, prepared as reported in Example 3, in aqueous solution, pH 7.2, for phosphate buffer, final osmolarity 300 $mOsmL^{-1}$, corrected with NaCl or another biocompatible osmolite containing dexamethasone 0.1% w/w.

Eyedrops 6—0.3% w/w CS/H-HA complex (stoichiometry CS/H-HA 0.5:1 w/w, prepared as reported in Example 3, in aqueous solution, pH 7.2, for phosphate buffer, final osmolarity 300 $mOsmL^{-1}$, corrected with NaCl or another biocompatible osmolite containing 0.1% w/w tetrazoline hydrochloride.

Example 8—Other Ophthalmic Formulations a) Ophthalmic ointment with a fatty matrix, containing in dispersed form a 300 mOsm aqueous solution, pH 7, of 1.0% w/w L/H-HA complex (stoichiometry L-HA/H-HA 0.5:1 w/w, prepared as reported in Example 1, containing one or more active ingredients of interest in the ophthalmic field.

b) Eye spray consisting of a 300 mOsm aqueous solution, pH 7, of 0.5% w/w L/H-HA complex (stoichiometry L-HA/H-HA 1.5:1 w/w, prepared as reported in Example 1, containing one or more active ingredients of interest in the ophthalmic field.

The invention claimed is:

1. An ophthalmic formulation comprising as active ingredients
cooperative hybrid complexes named L/H-HA characterized by high mucoadhesion and with a viscosity not exceeding 30 mPa, said cooperative hybrid complexes being obtainable by heating at 100-130° C. for 10-30 min a mixture of an aqueous solution containing low molecular weight hyaluronic acid (L-HA) or chondroitin (C), said C having an average molecular weight ranging from $1 \cdot 10^4$ to $1 \cdot 10^5$ Da and
hyaluronic acid (H-HA) having an average molecular weight at least 5 times higher than that of L-HA.

2. The ophthalmic formulation according to claim 1 in the form of eye drops, ointments or ophthalmic sprays.

3. The ophthalmic formulation according to claim 1 further comprising active ingredients selected from the group consisting of anti-glaucoma agents, mydriatic agents, mitotic agents, antimicrobial agents, non-steroidal anti-inflammatory drugs, antibiotics, beta-blockers and antihistamines, in addition to buffering agents, salts, osmolarity adjusting agents, preservatives, lenitives and rheological agents.

4. Method of treating dry eye syndrome with tear substitutes comprising the ophthalmic formulation according to claim 1.

* * * * *